United States Patent

Haas et al.

[11] Patent Number: 5,695,335
[45] Date of Patent: Dec. 9, 1997

[54] DENTAL IMPLANT

[75] Inventors: Franz Haas, Vienna; Rudolf Schneider, Heidenrelchstein, both of Austria

[73] Assignee: Mke Metall- Und Kunststoffwaren Erzeugungsgmbh, Heidenreichstein, Austria

[21] Appl. No.: 590,686

[22] Filed: Oct. 10, 1995

[30] Foreign Application Priority Data

Oct. 10, 1994 [AT] Austria ................ A1908/94

[51] Int. Cl.⁶ .................................. A61C 8/00
[52] U.S. Cl. .................................. 433/173; 433/169
[58] Field of Search .................. 433/169, 172, 433/173, 174, 177

[56] References Cited

U.S. PATENT DOCUMENTS

| 4,626,214 | 12/1986 | Artal | 433/169 |
|---|---|---|---|
| 4,631,031 | 12/1986 | Richter | 433/173 |
| 4,927,363 | 5/1990 | Schneider | 433/173 |
| 4,993,950 | 2/1991 | Mensor, Jr. | 433/173 |
| 5,040,982 | 8/1991 | Stefan-Dogar | 433/169 |
| 5,049,073 | 9/1991 | Lauks | 433/173 |
| 5,407,359 | 4/1995 | Balfour et al. | 433/173 |
| 5,571,016 | 11/1996 | Ingber et al. | 433/169 |

FOREIGN PATENT DOCUMENTS

| 312698 | 4/1989 | European Pat. Off. | 433/173 |
|---|---|---|---|
| 3811498 | 10/1989 | Germany | 433/169 |

*Primary Examiner*—Cary E. O'Connor
*Assistant Examiner*—Ralph A. Lewis
*Attorney, Agent, or Firm*—Herbert Dubno

[57] ABSTRACT

A primary implant member anchored in the jaw receives a secondary member which is held in the primary member by direct engagement by the head of a screw which bottoms in the primary member and O-ring bridges the radial play between these members in a dental implant. As a result, the retention of the secondary member does not depend on the state of the O-ring and the force with which the O-ring is held. Axial mobility and inclination of the secondary member is also permitted by the O-ring bridge.

7 Claims, 1 Drawing Sheet

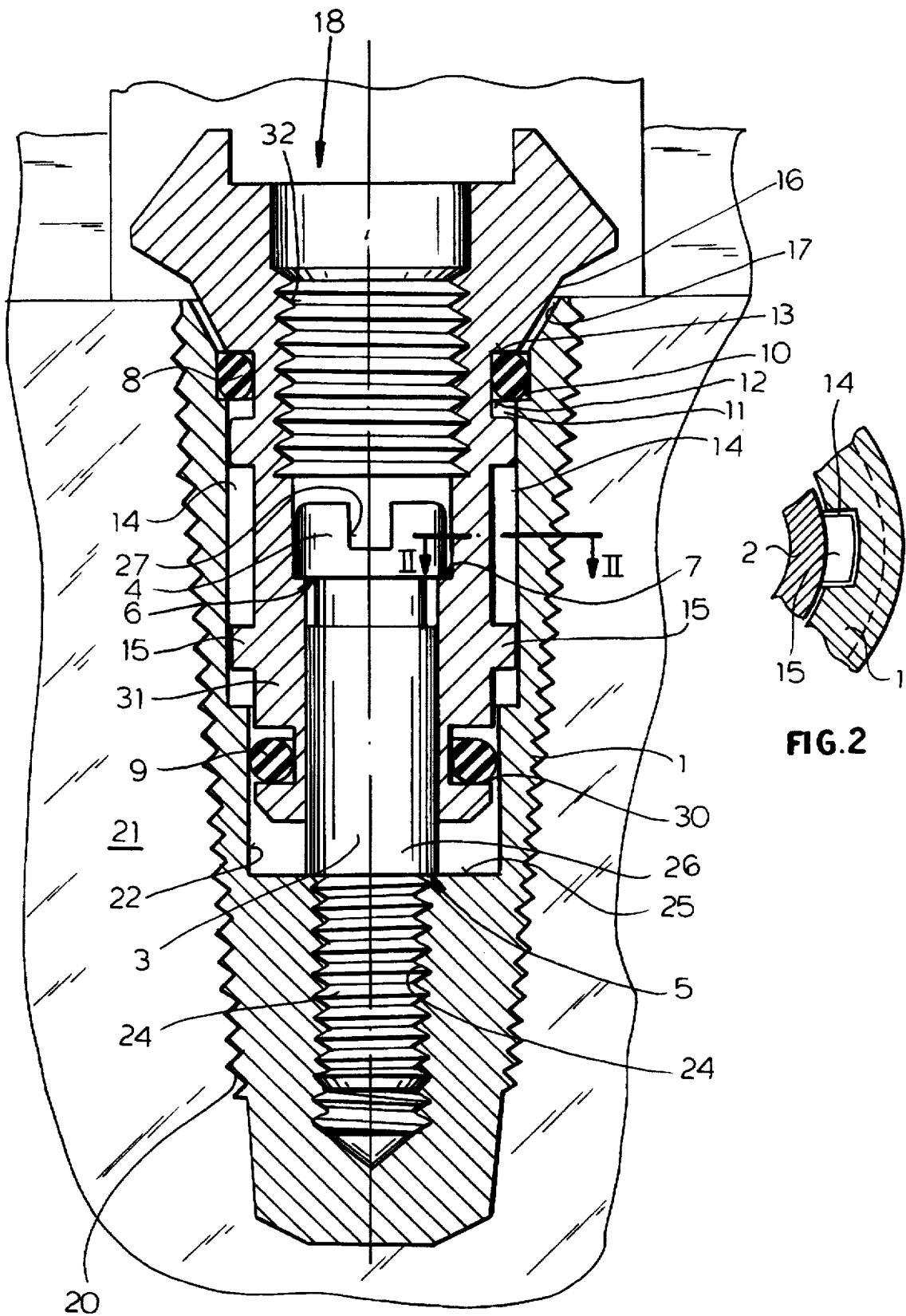

DENTAL IMPLANT

FIELD OF THE INVENTION

The present invention relates to a dental implant for the attachment of a dental prosthesis in a jawbone of a patient.

BACKGROUND OF THE INVENTION

The use of dental implants has gained increasing importance in recent years.

In one such implant, a primary implant member is anchored in a jawbone of the patient and receives a secondary implant member which is received with radial play in a recess of the primary member. An O-ring or the like can elastically bridge the radial play between the primary and secondary members.

The limited mobility of the secondary member serves to mimic the mobility possessed by natural teeth.

In one prior art construction, the stem of the secondary member which is received in the recess of the primary member has two annular grooves in which respective O-rings are seated and which index in respective annular grooves in the wall of the recess when the secondary member is inserted into the latter. This provides the appropriate elastic mounting.

A drawback of this system is that the secondary member is held in place only by the elastic O-rings and therefore there is a danger that this retention force may not be sufficient or that the O-rings will be damaged during insertion of the secondary member or shifted so that long term retention cannot be ensured.

If the stress on the O-ring is such that the retaining force is sufficient for long term retention with such a system, a later removal of the secondary member without removal of the primary member is often not possible.

There is also the danger that, upon assembly, the O-rings will be shifted from their proper positions. Finally, in spite of the presence of the O-rings, this construction has difficulties with sealing between the primary and secondary parts.

In another construction the O-ring is held in place by a screw via a compression ring with a conical surface. With this adjustable screw, the retaining force between the secondary member and the primary member can be adjusted with precision. However, the retention of the secondary member in the primary member is dependent upon the state of the O-ring so that it is necessary to set the yieldability at a desired level without exceeding it. Adjustment in this manner may not always be satisfactory and there is a tendency of the retention to depend upon aging and the like of the O-ring.

OBJECTS OF THE INVENTION

It is the principal object of the present invention to provide a dental implant which can have a certain degree of radial play and even axial play corresponding to the natural mobility of the teeth in the jaw without the drawbacks of earlier systems.

Another object of the invention is to provide a dental implant which has sufficient retention force, which nevertheless enables separation of the secondary member from the primary member without difficulty, and which yet does not depend exclusively on the state of the O-ring or O-rings for the retention capability.

Still another object of this invention is to provide an improved dental implant which has advantages over the earlier systems described but which is free from the disadvantages thereof.

SUMMARY OF THE INVENTION

These objects and others which will become apparent hereinafter are attained, in accordance with the invention by providing the screw so that it is driven until it abuts against a shoulder of the primary member or another stop therein while the head of the bolt directly engages a counter-surface of the secondary member so that the bolt directly prevents the secondary member from being withdrawn from the primary member. Stated otherwise, while the screw braces the secondary member against at least one O-ring which in turn is compressed against the primary member, the seating of the screw into abutment with the primary member and the direct engagement of the head of the screw against the counter-surface of the secondary member confines the axial play of the secondary member to movement into the primary member against the elastic O-ring and prevents the secondary member from being withdrawn from the primary member regardless of the state of the O-ring. The secondary member is braced against the O-ring and the primary member so that radial play is possible between the surface of the head of the screw and the counter-surface of the secondary member.

The secondary member can, with the dental prosthesis attached thereto, shift radially relative to the primary member against the compressed O-ring and move inwardly relative to the screw within the primary member in spite of the fact that the screw is fixed or has bottomed in the primary member. This is because the head of the screw does not draw the secondary member rigidly or solidly against the primary member but rather itself bottoms the primary member. The secondary member remains braced against the O-ring for limited axial and radial movement relative to the primary member.

Advantageously, the mouth of the recess is provided with a frustoconical surface which is complementary to the frustoconical surface of the head of the secondary member which receives the dental prosthesis and the space between these frustoconical surfaces is maintained when the O-ring is fully compressed by the bottoming of the screw against the primary member. This provides both a centering action and lateral bracing for the bite of the patient even in an inclined orientation of the dental prosthesis or inclined loading of the implant.

To afford the radial and axial mobility of the secondary member relative to the primary member, the O-ring can be held between opposite flanks of respective grooves in the two members receiving the O-ring adjacent the frustoconical surfaces. The recesses together form an annular chamber in which the O-ring is disposed. Depending upon the direction in which the secondary member is shifted relative to the primary member, radial and/or axial force is applied to the O-ring between the juxtaposed flanks of the grooves or the bases of the two grooves.

For centering the secondary member in the primary member in a load free condition of the prosthesis, a second O-ring can be provided in axially spaced relation to the first and in a groove of the stem of the secondary member and can engage a cylindrical wall of the recess. The symmetrically loaded O-rings can seal the two members relative to one another while providing the proper orientation of the two members in the unloaded state.

The implant is also provided with keying means preventing rotation of the secondary member in the primary member, preferably in the form of axial grooves in the primary member which are engaged by radial projections of the secondary member slidable in these axial grooves. The radial projections may be of limited axial length so that they allow the lateral tilting of canting of the prosthesis as well as the axial displacement so important for the natural mobility of the prosthesis. The formation of the exterior of the primary member, which enables it to be anchored in the jawbone can be a screwthread which enables the assembly of primary and secondary members to be inserted into a predrilled jawbone utilizing only a screwdriver. This screw thread can be a selftapping thread.

More specifically, an implant according to the invention can comprise:

an elongated primary implant member formed along an exterior thereof with means for seating the primary implant member in a jaw bone of a patient to be fitted with a dental prosthesis, the primary implant member being provided with a recess open at one end thereof, the recess having an internal thread and the primary implant member being formed with an annular shoulder;

an elongated secondary implant member received with radial play in the recess and having a portion outside the recess for receiving the dental prosthesis;

at least one elastic O-ring between the members bridging radial play between them;

keying means of the members securing the secondary implant member against rotation relative to the primary implant member while enabling the secondary member to slide axially in the primary implant member; and a screw having a head formed with a formation receiving a driving tool, a threaded shank threadedly engaging the internal thread, an abutment engageable with the shoulder upon screwing of the screw into the thread, and a stop surface of the head on a threaded shank side thereof engageable with a countersurface of the secondary member for preventing the secondary member from withdrawing from the primary member, bracing the secondary member against the O-ring in the primary member, and limiting axial play of the secondary member to movement against the O-ring into the primary member.

BRIEF DESCRIPTION OF THE DRAWING

The above and other objects, features, and advantages will become more readily apparent from the following description, reference being made to the accompanying drawing in which:

FIG. 1 is an axial section of a dental implant in accordance with the invention; and FIG. 2 is a section taken along the line II—II of FIG. 1.

SPECIFIC DESCRIPTION

In the drawing we show a dental implant, the primary part I of which is a frustoconical screw with an external thread 20 which can be of the selftapping type and is threaded into a hole previously drilled in a jawbone 21. The members of the implant can be composed of titanium.

Within the primary member 1 there is formed a recess 22 in the wall of which a pair of axial grooves 14 are provided and which is extended by an internally threaded bore 23.

The secondary member 2 of the implant is received with play within the recess and, in particular, with play in both the axial and radial directions.

More particularly, the secondary part II is held in the primary part I with a threaded bolt or screw 3 having a head 4 and a threaded shank 24, the latter being engaged in the threaded bore 23. The screw 3 is threaded into the primary member 1 until an annular shoulder 5 thereof bottoms against an annular shoulder 25 of the recess 22 at the top of the threaded bore 23. The shoulder 5 is formed at the distilled end of a shank 26 of the screw 3. The head 4 of the screw has an annular abutment surface 6 turned toward the threaded shank 24 which engages a counter-surface 7 of the secondary part II. The head 4 also has a slot 27 in which a screwdriver blade can fit.

Although the screw 3 bottoms against the primary member 1 and engages the annular surface 7, the secondary member 2 is braced against the primary member 1 only by O-rings 8 and 9.

The O-ring 8 is disposed in an annular chamber designed between 2 annular grooves 10 and 11 having radial flanks 12 and 13 which are opposite one another and which compress the O-ring 8 axially. The bases of the grooves 10 and 11 in the primary member 1 and the secondary member 2, respectively, compress the ring 8 in the radial direction. The flanks 12 and 13 allow the secondary member 2 to assume inclined positions relative to the primary member 1 as well.

The O-ring 9, received in a groove 30 of the stem 31 of the secondary member 2, engages the cylindrical wall of the recess 22 and serves to guide the secondary member 2 within the primary member 1 parallel to itself.

Radial projections 15 of the secondary member 2 engage in the axial grooves 14 to prevent angular displacement of the secondary member relative to the primary member. Since the grooves 14 are longer than the projections 15, the secondary member 2 can be axially shifted without rotating. The projections 15 also do not reach the floor of the groove 14 and thus have radial play therein to enable the inclined positioning of secondary member 2 within the primary member 1. With a purely axial force, the secondary member 2 simply squeezes the O-ring 8 until the frustoconical surface 16 comes to rest on the frustoconical surface 18. With inclined loading the O-rings 8 and 9 tend to center the secondary member 2. Thus all of the essential mobility for the teeth during eating can be provided, the dental prosthesis 18 being affixed to the secondary member 2, e.g. via the screwthread 32. Nevertheless, since the screw 3 bottoms on the primary member 1 and engages at 6, 7 the secondary member, the retention of the latter does not depend on the O-rings 8 and 9.

The implant, with the primary and secondary members previously attached together can be screwed into the prebored hole in the jawbone. Tightening can be accomplished via a screwdriver engaging the slot 27. The prosthesis can then be attached. During the implanting process, prior to application of the prosthesis and until the implant is fully grown in, usually a period of about 3 months, a plug or cap can be attached via the screw 32 to close the implant. After the implant has fully grown in, that cap can be removed and the prosthesis attached.

We claim:

1. An implant for anchoring a dental prosthesis comprising:

an elongated primary implant member formed along an exterior thereof with means for seating said primary implant member in a jaw bone of a patient to be fitted with a dental prosthesis, said primary implant member being provided with:

a recess open at one end thereof, said recess being formed with a mouth formed as a frustoconical surface at said one end and with an annular shoulder spaced axially from said on end, and a bore extending axially from said annular shoulder toward an end of said primary implant member opposite said one end and having an internal thread;

an elongated secondary implant member formed with a respective frustoconical surface an a received with radial play in said recess, so that said frustoconical surfaces of the mouth and second implant member are complementary to one another, said second implant member having a portion outside said recess for receiving said dental prosthesis and being formed with a longitudinal thoroughgoing opening;

at least one elastic O-ring between said members bridging radial play between them and holding said frustoconical surfaces in spaced-apart relationship;

keying means of said members securing said secondary implant member against rotation relative to said primary implant member while enabling said secondary member to slide axially in said primary implant member; and a screw received in said opening of said secondary implant member and having a head formed with a formation for receiving a driving tool, a threaded shank threadedly engaging said internal thread of said bore, an abutment engageable with said shoulder upon screwing of the screw into said thread, and a stop surface of said head on a threaded shank side thereof engageable with a countersurface of said secondary member for preventing said secondary member from withdrawing from said primary member, bracing said secondary member against said O-ring in said primary member, and limiting axial play of said secondary member to movement against said O-ring into said primary member.

2. The implant defined in claim 1 wherein said O-ring lies in respective annular grooves formed in said primary member and said secondary member adjacent the respective frustoconical surfaces, said grooves having oppositely directed flanks engaging said O-ring between them.

3. The implant defined in claim 2, further comprising another O-ring axially spaced from the first-mentioned O-ring bridging radial play between said members.

4. The implant defined in claim 1 wherein said keying means includes axially extending grooves formed in a wall of said recess, and radial projections on said secondary member slidably engageable in said axially extending grooves.

5. The implant defined in claim 1, further comprising another O-ring axially spaced from the first-mentioned O-ring bridging radial play between said members.

6. The implant defined in claim 1 wherein said keying means includes axially extending grooves formed in a wall of said recess, and radial projections on said secondary member slidably engageable in said axially extending grooves.

7. The implant defined in claim 1 wherein said formation is a slot for receiving a screwdriver blade.

* * * * *